(12) United States Patent
Prevost et al.

(10) Patent No.: US 7,875,027 B2
(45) Date of Patent: Jan. 25, 2011

(54) AUTOCLAVEABLE HANDLE WITH STRIPPING MECHANISM TO ATTACH A DISPOSABLE CONNECTING CABLE

(75) Inventors: Julien Prevost, Memphis, TN (US); James P. Duncan, Southaven, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 943 days.

(21) Appl. No.: 11/789,920

(22) Filed: Apr. 26, 2007

(65) Prior Publication Data
US 2008/0269736 A1 Oct. 30, 2008

(51) Int. Cl.
*A61B 18/18* (2006.01)
(52) U.S. Cl. ............... 606/41; 16/110.1; 16/111.1
(58) Field of Classification Search ............ 29/729; 16/110.1, 111.1, 412–414, 422, 426, 430, 16/433, 436, 441; 606/41; 439/784
See application file for complete search history.

(56) References Cited

U.S. PATENT DOCUMENTS

| | | | |
|---|---|---|---|
| 4,207,903 A | 6/1980 | O'Neill | |
| 5,196,007 A * | 3/1993 | Ellman et al. | 606/32 |
| 5,679,026 A * | 10/1997 | Fain et al. | 439/651 |
| 5,830,005 A * | 11/1998 | Watanabe | 439/418 |
| 5,944,562 A | 8/1999 | Christensson | |
| 6,231,571 B1 | 5/2001 | Ellman et al. | |
| 6,264,652 B1 | 7/2001 | Eggers et al. | |
| 6,461,350 B1 | 10/2002 | Underwood et al. | |
| 6,743,055 B1 * | 6/2004 | Flynn et al. | 439/651 |

* cited by examiner

*Primary Examiner*—Linda C Dvorak
*Assistant Examiner*—Jaymi Della

(57) ABSTRACT

Embodiments of a handle for use in a surgical tool that uses electricity is disclosed. In one embodiment, the handle is autoclaveable and reusable, and includes connections between an electrical cable (e.g. for providing electrical energy and/or transmitting electrical signals) and an operating end of the tool. An insert member having arms for stripping wire or cable electrically connects the cable and the operating end of the tool, and a set screw may be provided to hold the cable in place. A clip member may also be provided to hold the handle to the rest of the tool. Method for using and assembling handle embodiments are also described.

31 Claims, 8 Drawing Sheets

AUTOCLAVEABLE HANDLE WITH STRIPPING MECHANISM TO ATTACH A DISPOSABLE CONNECTING CABLE

The present disclosure relates to tools useful in surgery, and in particular to tools having electrical cables for providing current to an operating portion, for obtaining data from a surgical site, or for other purposes.

In the field of surgery in general, and orthopedic surgery in particular, it is well-known to use a variety of tools to accomplish tasks as varied as assessment or diagnosis, tissue removal or repair, and many other tasks. In the past, such tools have been mechanical in nature, with particular structures designed to impart mechanical advantage or mechanical change to tissues, or to use physical structures to obtain information through moving tissue, mechanical measurement, or other physical methods. More recently, tools using electrical signals have been developed to provide current as a corrective or therapeutic sense, as in cauterization or tissue ablation, to provide measurements or other data from tissue, or for other purposes.

Such electrical tools will include one or more electrodes for insertion into the tissue or surgical site of interest to the surgeon. To protect the surgeon's hand, a housing for the electrodes and/or a disposable handle for the housing or tool has been provided, and in many cases the tool itself has been made disposable. To decrease costs associated with these tools and the procedures in which they are used, it would be helpful to have a reuseable and sterilizable handle that connects a cable to the electrical operating portions of a tool.

SUMMARY

Among other things, there are disclosed embodiments of a handle for a surgical tool with a body portion having an exterior surface and first, second and third holes each having separate openings through the exterior surface, the second hole being sized to accommodate an electrical conductor, and the third hole being at least partially threaded. In the first hole an insert member may be removably placed, which has a cap portion that is substantially flush with the exterior surface of the body portion when placed in the first hole, and a pair of arms distal of the cap for stripping covering from an electrical conductor. A set screw may be threaded into the third hole. In certain embodiments, the first hole and third hole communicate with the second hole, and neither of the first hole and third hole are parallel or concentric with the second hole. Embodiments of such a handle may have a body that includes an extension having an aperture that communicates with the second hole, with a substantially C-shaped clip around at least part of the extension. At least a portion of the exterior surface of the body can be substantially spherical, and the extension can extend substantially radially from that spherical surface. A washer having an opening for a cable can be fitted into the second hole.

In certain embodiments, the second hole can be oriented substantially radially with respect to a substantially spherical exterior surface of the body, and the first hole and third hole may be oriented non-radially with respect to the exterior surface and substantially perpendicular to the second hole. The first and third holes may meet at substantially the same point along the second hole. The cap of the insert member may be have a perimeter that is part convex and part concave. The insert member may include a medial portion with at least one hole between the cap and the arms. At least the body of said handle may be made of a substance that is autoclaveable without substantial change in its physical characteristics, such as polyoxymethylene, which substance may be compressible.

Embodiments of a tool for use in spinal orthopedic surgery are also disclosed, using a handle as described above, and having a housing with an operating end with at least one electrode and at least one conductor electrically connected to the at least one electrode and electrically connected to the insert member of the handle. A cable is connected to the handle so as to extend through the handle's second hole, and it may have a first end with a plug, a second end, and at least one electrical conductor that is electrically connected to the insert member of the handle. An electrical power source may be provided, connected to the plug, or a detector for detecting and analyzing electrical signals may be provided and connected to the plug. The handle may include an aperture communicating with the second hole of the handle, with the housing insertable into that aperture. At least a portion of the exterior surface of the handle can be substantially spherical, and the handle can include an extension through which the aperture runs extending substantially radially from the exterior surface. A clip having an internal diameter smaller than at least a portion of the extension can also be provided, wherein the clip retains the housing within the handle.

In other embodiments, a handle for a surgical tool that uses electricity is disclosed, which includes a body portion having at least a part that is substantially spherical, an extension portion adapted to connect to a tool shaft and having at least a part that is substantially cylindrical, and an insert member removably inserted into the body portion. The insert member has a cap portion with a perimeter that has a convex portion and a concave portion and a distal portion including two arms configured for stripping wire or cable. The body portion includes a hole adapted to accommodate a wire or cable, and the body enables electricity to be passed from a wire or cable in the hole to a shaft extending from the extension. At least a portion of the insert member can be made of a electrically-conductive material. The body can include a second hole that is at least partially threaded and communicating with the hole that is adapted to accommodate a wire or cable, and the handle can further include a set screw threaded into that second hole to a position in or adjacent to the hole that is adapted to accommodate a wire or cable. A washer that accommodates the cable or wire can be inserted into its hole. Additionally, the extension of the handle can include a channel in which a clip member can be inserted. That channel may have a bottom surface that defines a minor diameter of the extension, the clip member may be substantially C-shaped and define an inner diameter, and that inner diameter can be smaller than the minor diameter. The handle can be autoclaveable (e.g. made of polyoxymethylene) without substantial change in its physical characteristics, and may be made out of a compressible substance.

Methods are also disclosed, such as a method including providing a tool with a handle, a cable connected to the handle, and an operating portion connected to the handle, the operating portion having electrodes electrically connected to the cable through the handle, the handle including an insert member having an electrically conductive portion that is electrically connected to the cable and the operating portion and a set screw threaded into the handle and holding the cable with respect to the handle. The method can further include loosening the screw from the handle, removing the cable from the handle, autoclaving the handle, inserting a cable into the handle so that the cable is electrically connected to the operating portion, and tightening the screw in the handle to hold the cable in the handle. The cable in the inserting step may be substantially the same cable as the cable in the removing step, so that essentially the same cable that is removed from the handle is replaced in the handle. A portion of the cable can be cut off and an end of the cable can be stripped prior to the inserting step. The insert member may have a portion adapted to strip cable, and the insert member can be removed from the handle, the insert member can be used in the stripping step, and the insert member can be replaced in the handle. In some embodiments, the operating portion can be removed from the handle prior to the autoclaving step, or the handle can include a clip that holds the operating portion with respect to the handle, and the step of removing the operating portion can include disconnecting the clip from the handle.

DESCRIPTION OF THE ILLUSTRATED EMBODIMENTS

Figure 1:
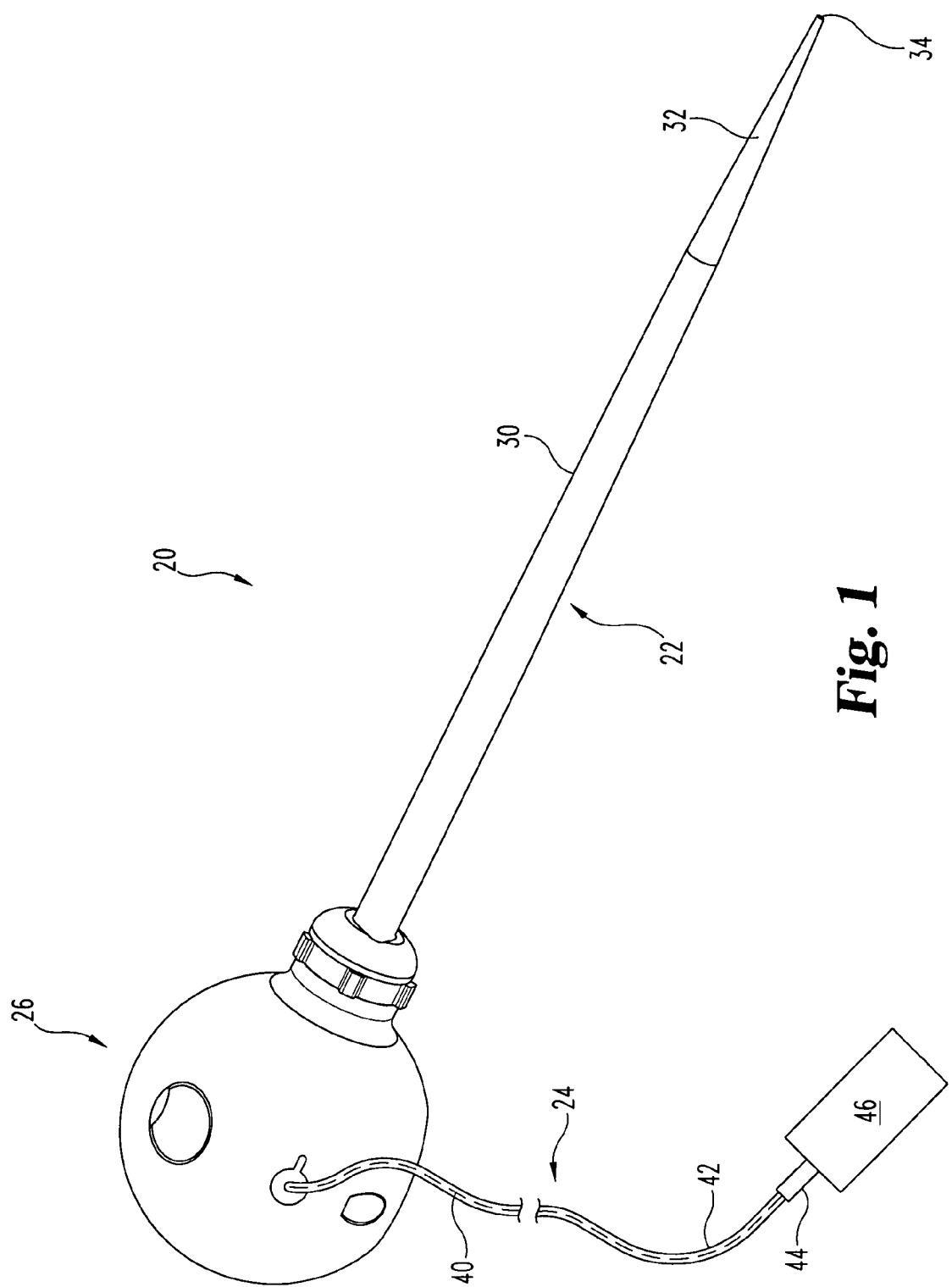
FIG. 1 is a perspective view of an embodiment of a tool with an embodiment of a handle.
Figure 2:
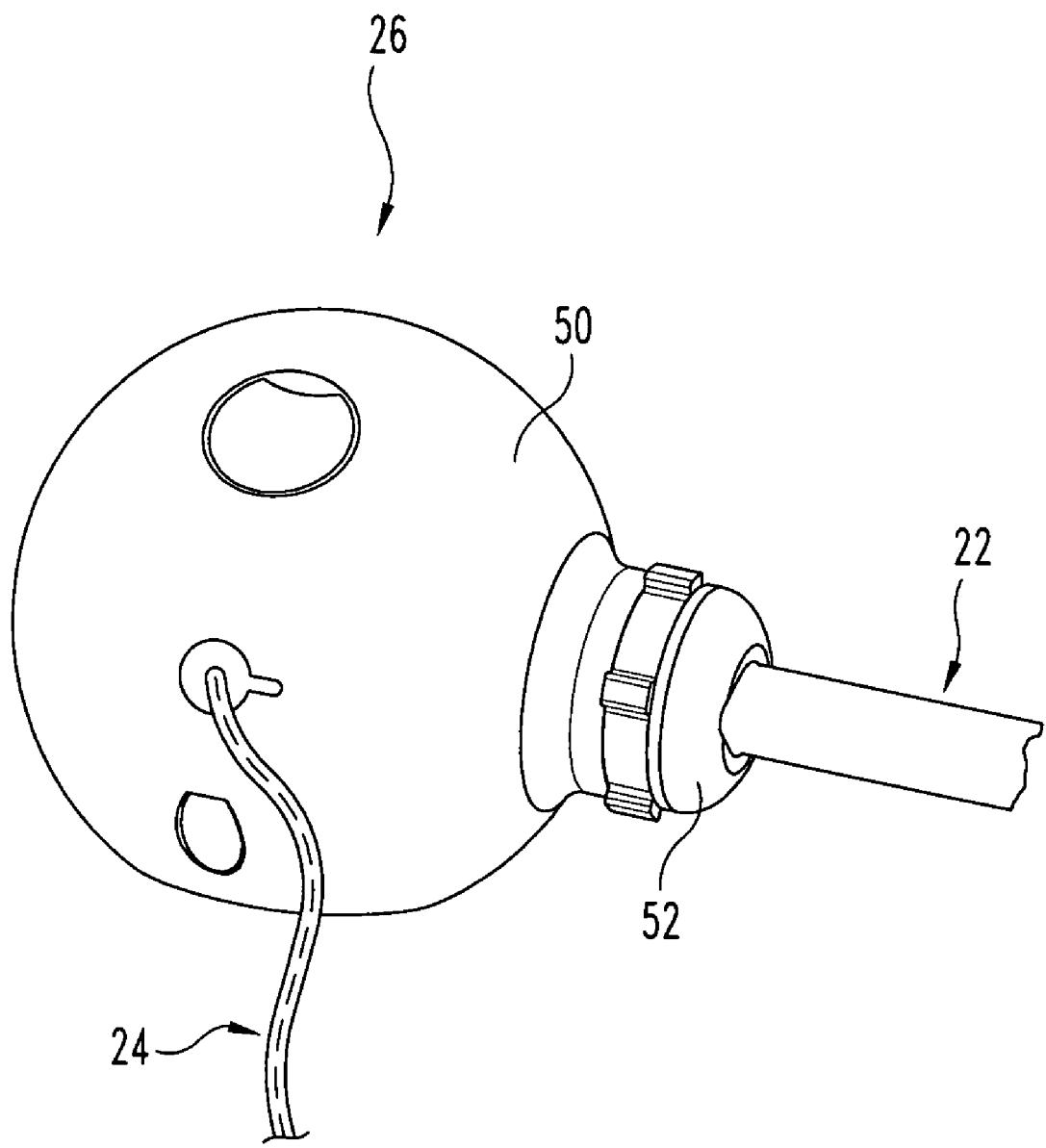
FIG. 2 is a magnified side view of part of the embodiments shown in FIG. 1.
Figure 3:
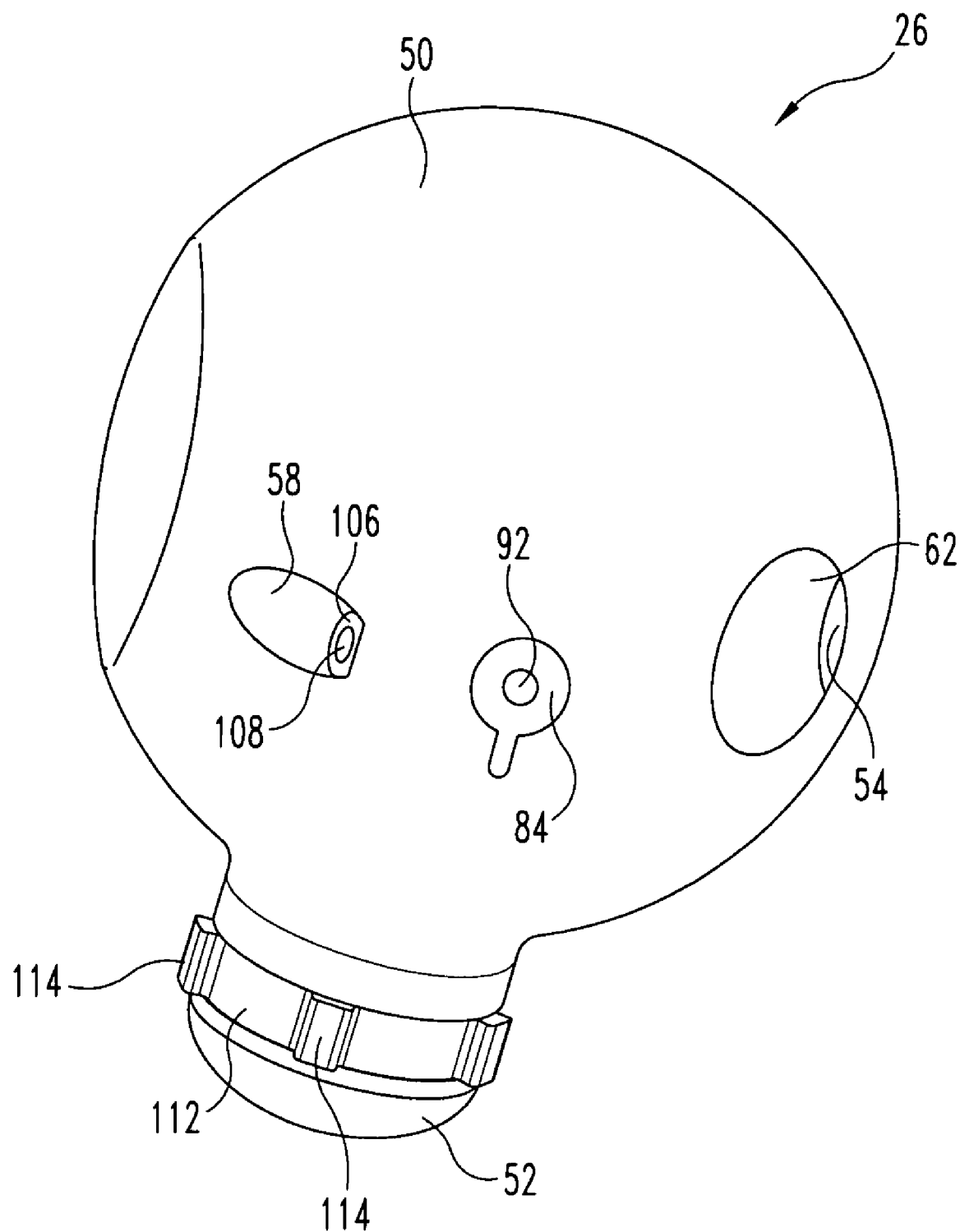
FIG. 3 is a perspective view of the embodiment of a handle shown in FIG. 1.
Figure 4:
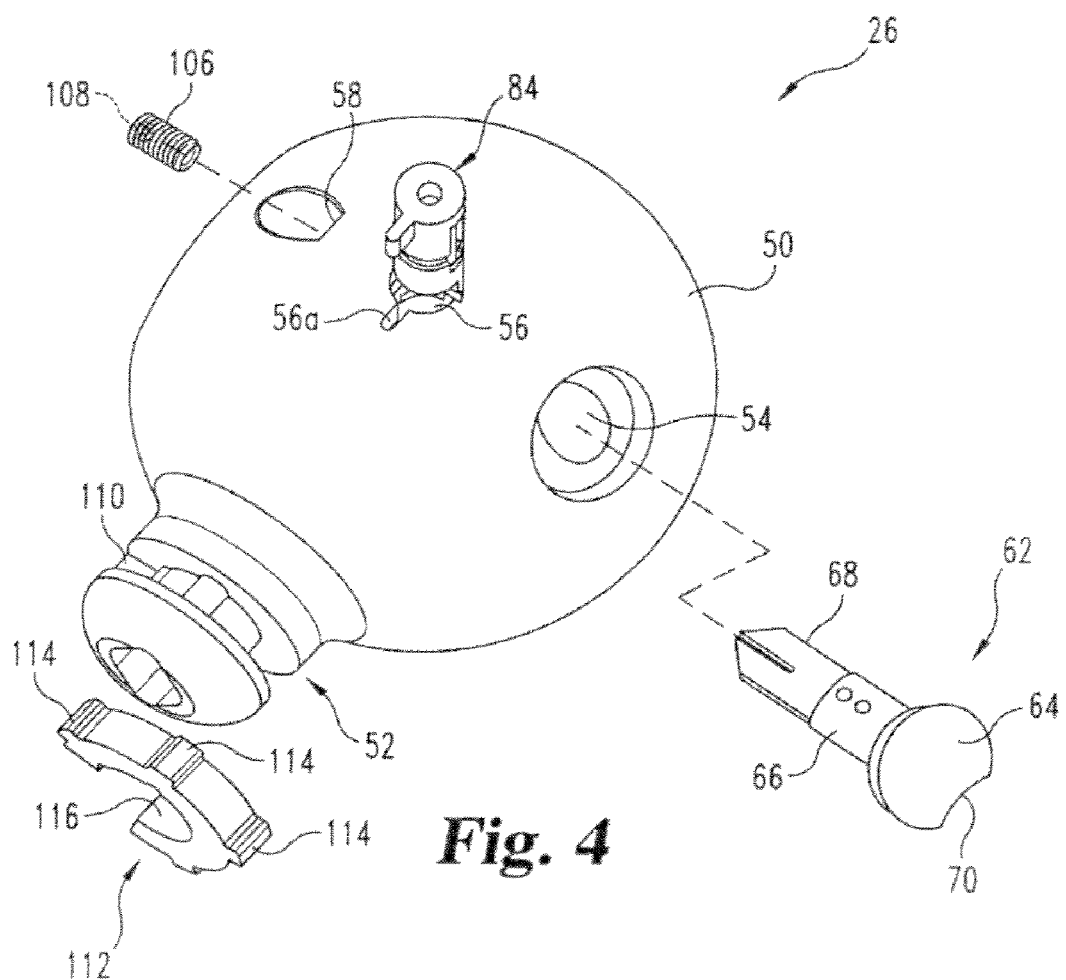
FIG. 4 is an exploded view in perspective of the embodiment of a handle shown in FIG. 1.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein being contemplated, as would normally occur to one skilled in the art to which the disclosure relates.

Referring generally to the figures, there is shown an embodiment of a tool 20 having an operating portion 22, a connecting cable 24, and a handle 26 that connects cable 24 to operating portion 22. In this embodiment, tool 20 may be any of a number of types of tools that include electrodes or other electrical components for use in surgery.

Operating portion 22 in the illustrated embodiment is the generally elongated structure of a probe or needle, part of which can be inserted to a surgical site while the surgeon's hand remains substantially outside the patient. In that embodiment, operating portion 22 includes a housing or sleeve 30 and an electrode end 32. End 32 may have one or more electrodes 34 connected to an end of housing 30, which electrodes 34 are configured to provide the desired current to or data from adjacent tissue. One or more conductors extend from electrodes 34 to or into handle 26 for conveying electrical energy to electrodes 34. In one embodiment, housing 30 may be made of a metal or other conductive material and may act as such a conductor. In other embodiments, wires, or other conductors may be placed within housing 30 or under a surface layer of housing 30 to run from electrodes 34 to handle 26. Electrodes 34 may be configured as may be desired for a particular purpose, and in the illustrated embodiment come to a point or edge befitting a probe or needle. The part of electrodes 34 that connect to housing 30 may have a rounded or cylindrical portion that fits in housing 30, and may slope or narrow along opposite sides to produce substantially flat electrodes 34. Housing or sleeve 30 is substantially hollow with a longitudinal lumen, in one embodiment, and in other embodiments (e.g. those in which conductors extend through or along housing 30) it may be substantially solid.

Figure 9:
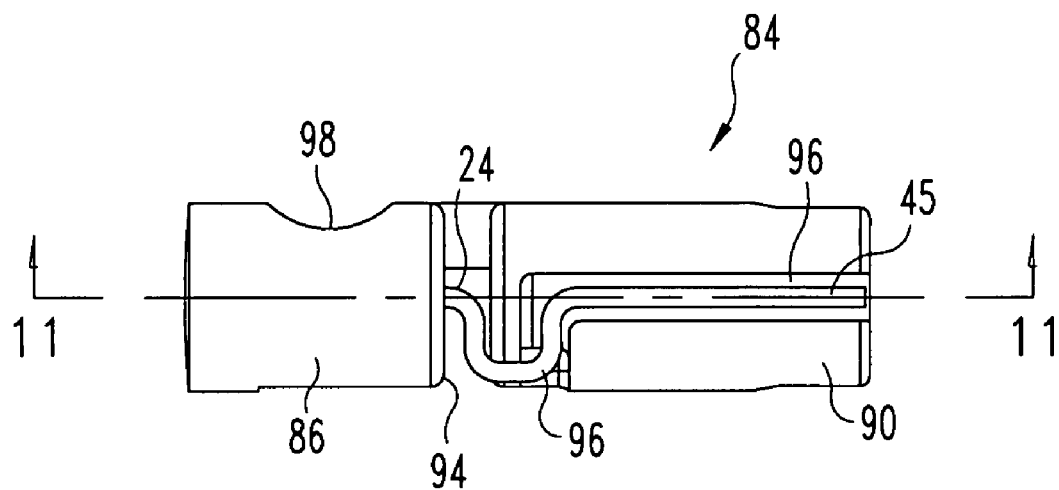
FIG. 9 is a top plan view of part of the embodiment of a handle shown in FIG. 1.
Figure 10:
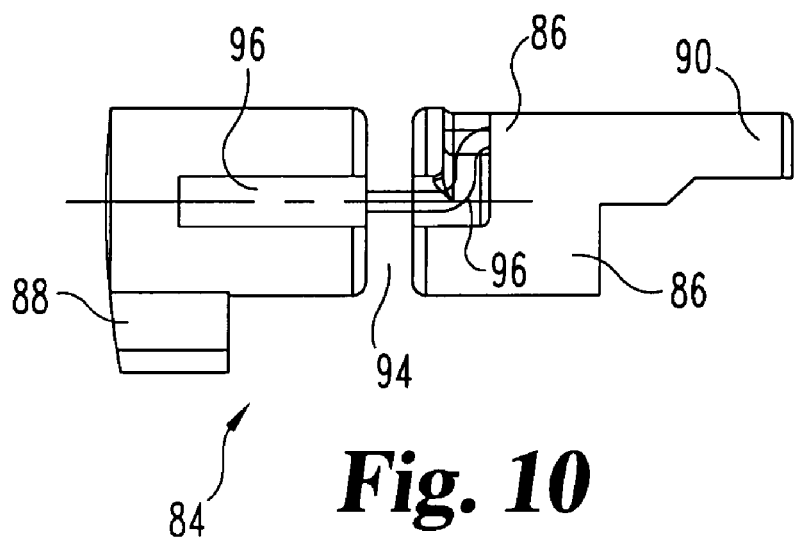
FIG. 10 is a side elevational view of part of the embodiment of a handle shown in FIG. 1.
Figure 11:
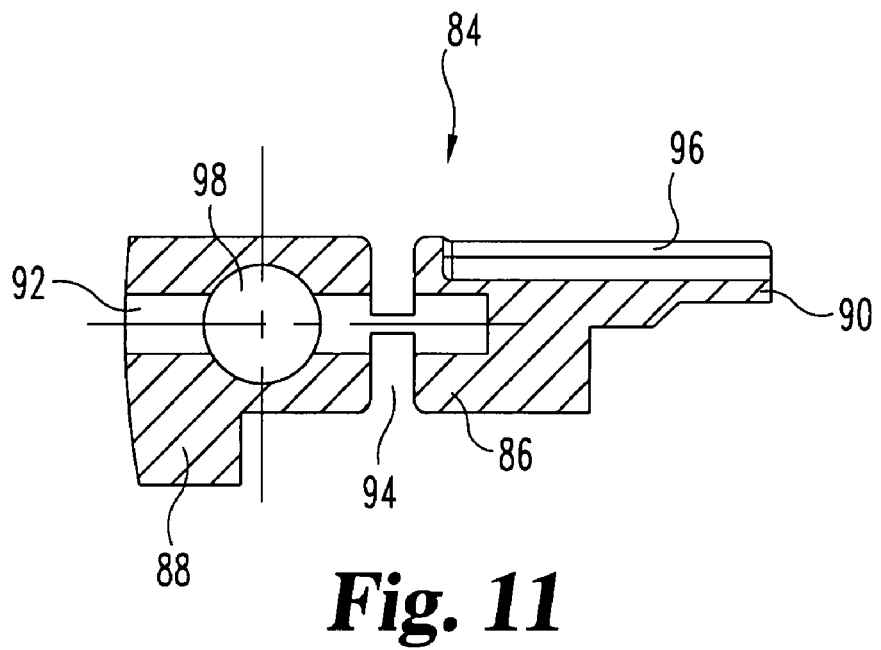
FIG. 11 is a cross-sectional view of the embodiment shown in FIG. 9, taken along the lines 11-11 in FIG. 9 and viewed in the direction of the arrows.
Figure 12:
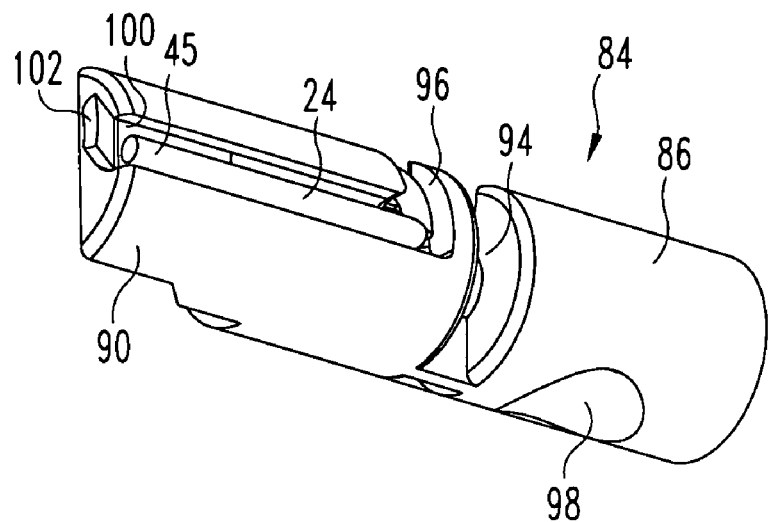
FIG. 12 is a perspective view of part of the embodiment shown in FIG. 9, with additional structure.

The illustrated embodiment of cable 24 has an internal conductor 40, an external covering or coating 42, and a distal connecting plug 44. The end 45 (FIG. 9) of cable 24 opposite plug 44 may have a connecting plug in some embodiments, but in the illustrated embodiment it is simply an end of the cable. Conductor 40 may be one or more wires either separate from or wound with each other and made of a conducting material such as copper. Covering or coating 42 is preferably a flexible plastic or other non-conducting material that shields conductor 40 from other conductors, from the surgeon's or others' hands, or other items. Plug 44 is electrically connected to conductor 40, and is configured to connect conductor 40 to another conductor or device 46 for supplying electric current to conductor 40, for accepting electrical signals from conductor 40, or for other purposes. Thus, device 46 may be a power source, a detector for electronic signals or similar apparatus. Accordingly, plug 44 may have several contacts, e.g. one for transmitting energy on to conductor 40 for transmission to electrodes 34, and/or one or more for transmitting electrical signals from electrodes 34 (by way of conductor 40) to an analytical device, data collector, or other instrument.

Handle 26, in the illustrated embodiment, has a substantially spherical body 50 and a substantially cylindrical extension 52. The substantially spherical shape of body 50 has been found to be easy to hold in both the palm of the hand and by the fingers, and thus is a shape that allows both steady gripping by most or all of the hand as well as delicate maneuvering by using the fingers or fingertips, while cylindrical or block-shaped handles may not permit such advantages. The substantially cylindrical shape of extension 52 has been found to enable relatively easy connection to housing 30. Nonetheless, it will be seen that other shapes could be used for the body 50 and extension 52 of handle 26.

Figure 5:
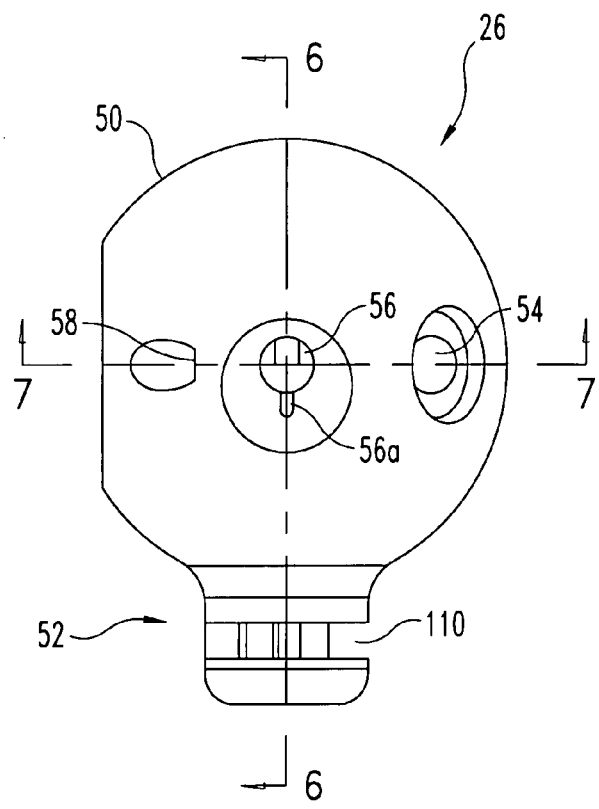
FIG. 5 is a side view of part of the embodiment of a handle shown in FIG. 1.
Figure 6:
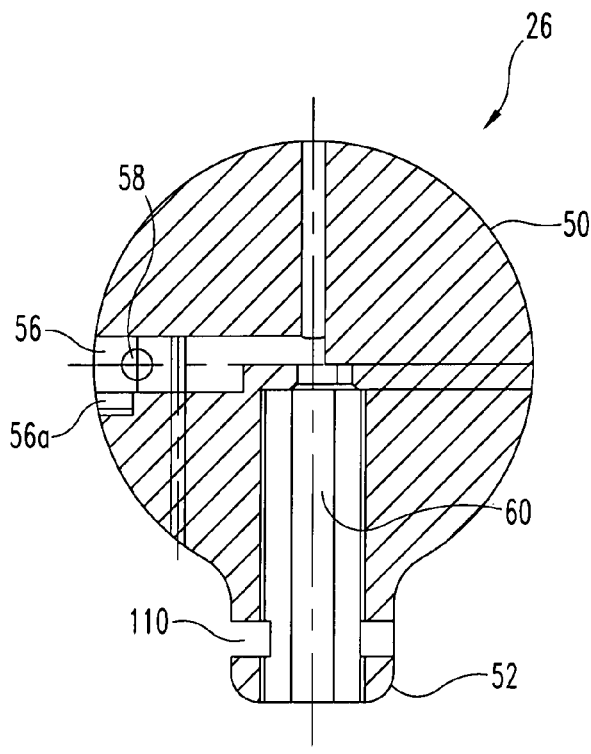
FIG. 6 is a cross-sectional view of the embodiment shown in FIG. 5, taken along the lines 6-6 in FIG. 5 and viewed in the direction of the arrows.
Figure 7:
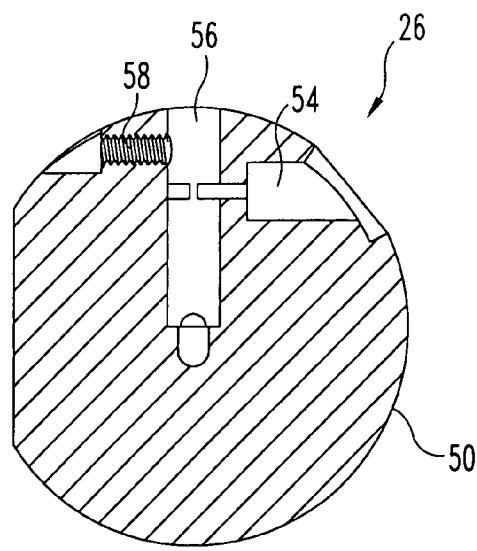
FIG. 7 is a cross-sectional view of the embodiment shown in FIG. 5, taken along the lines 7-7 in FIG. 5 and viewed in the direction of the arrows.
Figure 8:
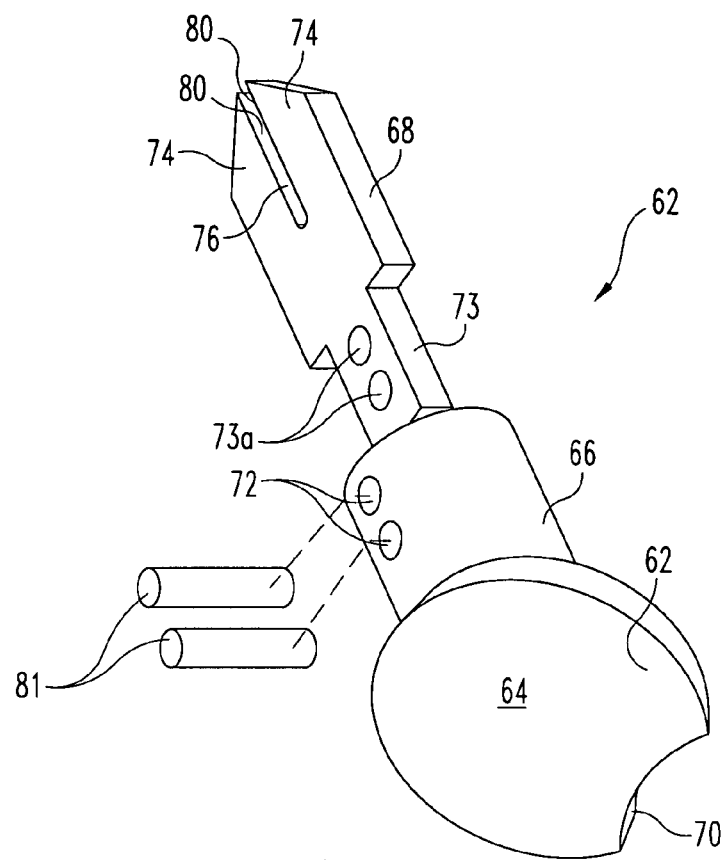
FIG. 8 is an exploded view in perspective of part of the embodiment of a handle shown in FIG. 1.

Body 50, in the illustrated embodiment, includes holes 54, 56 and 58 that extend at least part of the way through body 50. As will be seen in FIG. 5, holes 54, 56 and 58 substantially intersect in this embodiment, and they also intersect with an aperture 60 that extends through body 50 and out of extension 52. Hole 54 has a substantially oval opening in the surface of body 50 that narrows to a smaller diameter within body 50. Hole 56 has a generally substantially circular opening with a hole extension 56a. Hole 56 is oriented at least approximately toward a center of body 50 (e.g. substantially radially where body 50 is a sphere. Hole 58 has an oval shaped opening in the surface of body 50, and hole 58 is at least partially threaded. Holes 54 and 58 extend through the surface of body 50 in a direction that is not radial and that is generally toward hole 56. In other words, in this embodiment holes 54 and 58 are oblique to the tangent of a substantially spherical body 50.

Within hole 54, in this embodiment, there is found an insert 62 that includes a cap 64 attached to a medial portion 66 and a distal portion 68. Cap 64 has a perimeter or outer surface that is convex and somewhat oval-shaped and sized to fit within the opening of hole 54 in the surface of body 50, and to prevent insert 62 from going too far into body 50. Cap 64 is oblique, in this embodiment, to a longitudinal axis of medial portion 66 and distal portion 68, so that cap 64 can rest substantially flush with the exterior surface of handle 26. In this particular embodiment a concave portion 70 is in one side of cap 64 to assist a surgeon or other user in removing insert 62 from hole 54. Medial portion 66 is substantially cylindrical in this embodiment, and includes a set of holes 72 part way or all the way through medial portion 66. The set of holes 72 numbers two holes in this embodiment, although it will be seen that one or more holes 72 may be provided in the set, or in other embodiments holes 72 may be omitted. Distal portion 68 includes a connecting portion 73 having one or more holes 73a and pair of arms 74 separated by a slot 76, which arms can be configured as a wire cutting and/or stripping device. Internal edges 80 of each arm 74 may be relatively sharp to make wire stripping or cutting easier. Connecting portion 73 is inserted into medial portion 66 so that at least one hole 72 and at least one hole 73a are substantially aligned, and one or more pins 81 are inserted through such aligned hole(s) 72 and 73a. In this embodiment, one or both of medial portion 66 and distal portion 68 are metal or other electrically-conductive material, for connecting cable 24 to electrodes 34 of housing 30.

Hole 56 is occupied by a cable holder 84, which has a roughly cylindrical body 86 with a radial projection 88 that fits into hole portion 56a, and a part-cylindrical extension portion 90. A substantially-centered aperture 92 runs through at least part of body 86, and a slot 94 is approximately perpendicular to aperture 92 in this embodiment. An external groove 96 substantially parallel to aperture 92 runs across slot 94 and along a side and top portion of body 86 and into extension portion 90. A side opening 98 communicates with aperture 92. A connector 100 is placed in groove 96. In this embodiment, connector 100 is of a conductive material and includes an extending tongue 102 and a portion that extends through groove 96 and across slot 94. Tongue 102 or other part of connector 100 electrically connects via aperture 60 to conductors in or on housing 30, so that electricity and/or electronic signals may pass between cable 24 through aperture 60 to housing 30 and electrodes 34. The rest of cable holder 84 is made of a non-conductive material, in this embodiment. Cable holder 84 is removable from and insertable into hole 56 of body 50, with projection 88 fitting in opening 56a to ensure proper orientation and inhibit rotation of holder 84 in hole 56. Aperture 92 may be sized so that there is some or substantial friction between its edges and cable 24 (i.e. diameter of aperture 92 is about the same or slightly smaller than diameter of cable 24), as one way of impeding or preventing accidental disconnection of cable 24 from handle 26.

Hole 58 is internally threaded in this embodiment, and a set screw 106 is threaded into it. Hole 58 intersects with holes 54 and 56 at about the same point, so that set screw 106 can be threaded in far enough to abut or enter hole 56 and perhaps hole 54. Set screw 106 may be used to hold cable 24 within handle 26, and in the illustrated embodiment a bare portion of cable 24 can be sandwiched between screw 106 and insert 62, to make an electrically-conductive connection. Set screw 106 is externally threaded and includes an internal print 108 for receiving a turning tool (not shown). Print 108 is hexagonal in the illustrated embodiment, but may be square or otherwise configured to accommodate the head of other types of turning tools.

Extension 52, in the illustrated embodiment, has a part of aperture 60 that extends through, as well as an exterior channel 110. A substantially C-shaped clip 112 is provided to occupy at least part of channel 110. In the illustrated embodiment, a set of grips 114 extend from an otherwise substantially part-cylindrical clip 112, and the parts of clip 112 between or adjacent to grips 114 are sized to be substantially flush with the exterior surface of extension 52 when clip 112 is within channel 110. Further, the illustrated embodiment of clip 112 extends about two-thirds of the way around channel 110. The interior diameter 116 of clip 112 is, in the illustrated embodiment, smaller than a minor diameter of the part of extension 52 at the bottom of channel 110, so that when clip 112 is inserted into channel 110, clip 112 exerts a compressive force on the part of extension 52 at the bottom of channel 110.

Aperture 60 of handle 26 extends through extension 52 and into body 50, as noted above. Housing or sleeve 30 is inserted into aperture 60 through extension 52, and clip 112 is inserted into channel 100 to hold housing 30 with respect to handle 20. In certain embodiments, housing 30 may have an upper lip or channel that has an outer diameter that is at least slightly larger than the inner diameter 116 of clip 112. Clip 112 ensures that housing 30 cannot be removed from handle 26, in this embodiment, without removing clip 112 from extension 52 of handle 26. With housing 30 so connected to handle 26, conductors 34 in housing 30 are in electrical contact with insert 62, which connects to cable 24.

Handle 26 is autoclaveable and reusable in this embodiment, in order to increase efficiency and reduce waste. Thus, handle 26 should be constructed of materials that will withstand the high heat and pressure of common autoclaves or other sterilization machines or processes. Metals may be used for handle 26. In a particular embodiment, handle 26 may be made of plastics such as polyoxymethylene or POM (e.g. material sold by DuPont under the DELRIN® trademark), which is a lightweight, low-friction, and wear-resistant plastic capable of operating in temperatures in excess of 90 degrees Celsius. By making handle 26 out of a nonmetallic material such as POM, the conductors (e.g. cable 24, insert 62 and interfaces between one or both of them and housing 30 of the probe, needle, or other tool 20) are shielded from shorts or other undesirable interference with the electric energy or signals passing through handle 26.

Assembly of handle 26 and tool 20 allows a continuous electrical path between operating end 32 of operating portion 22 and plug 44 of cable 24. Insert 62 can be used, as indicated above, to strip the end 45 of cable 24 and expose the end(s) of conductor(s) 40 in cable 24, for example by inserting end 45 of cable 24 between arms 74 of insert 62 so that edges 80 slice into covering 42 of cable 24 and allow one to remove a portion of covering 42. Such stripping can occur before cable 24 is inserted into hole 56 of handle 26, or with cable 24 already through hole 56 and extending through handle 26 and out of hole 54 or aperture 60. Once cable 24 is inserted into hole 56 and has a bare connecting end 45, those bare conductor(s) 40 can be wrapped around or otherwise connected to distal portion 68 or other conductive portion of insert 62. Insert 62 can then be replaced in hole 54 of handle 26. By replacing insert 62 in hole 54, conductor(s) 40 and conductive part (e.g. distal portion 68) of insert 62 are positioned in handle 26 and proximate or adjacent to aperture 60. To hold cable 24 in a particular position, set screw 106 is tightened in hole 58 against cable 24, e.g. to hold cable 24 against a conductive part of insert 62.

Housing 30 is inserted into aperture 60 through extension 52 of handle 26, so that electrode(s) or conductor(s) 34 of operating portion 22 are in contact with one or both of conductor(s) 40 of cable 24 and a conductive portion of insert 62. Clip 112 is fitted into channel 100 to retain housing 30 in aperture 60. Electrode(s) or conductor(s) 34 of housing 30 may have one or more extending ends that can be attached to or plugged into holes 72 in medial portion 66 of insert 62. Alternatively, the inside of hole 54 and/or aperture 60 can form sockets having metal linings or electrical connections to which conductor(s) 34 of operating portion 22 and insert 62 are engageable. It will also be seen that conductor(s) 40 of cable 24 may be pinned by insert 62 to a socket or conductor, rather than being inserted in or wrapped around insert 62.

In these ways, a complete electrical path is created between end 32 of operating portion 22 and plug 44 of cable 24. Energy can be passed from a source through plug 44 and conductor(s) 40 of cable 24, via insert 62, and into conductor(s) 34 of operating portion 22 to end 32. Signals generated by operating end 32 can be passed through conductor(s) 34, via insert 62, to conductor(s) 40 and plug 44 of cable 24. Plug 24 is connected to an energy source for providing energy or a reading or analysis device (either of which are indicated schematically in the drawings as device 46) to receive signals and provide the surgeon with information. If a cable 24 has multiple conductors 40 shielded from each other, then energy can be provided to the operating end 32 along one conductor 40, and signals can be returned through cable 24 via another conductor 40.

For resterilization and reuse, cable 24 can be removed from handle 26, and handle 26 can be disassembled from housing 30. Set screw 106 is loosened, and if necessary cable 24 is disengaged from around insert 62. Cable 24 can then be pulled out of hole 56 and, if necessary, a portion of cable 24 can be clipped off. Thus, parts of cable 24 can be removed that have been contaminated by use in surgery and cannot be autoclaved or otherwise cleaned properly, and the remainder of cable 24 can be reused. Clip 112 is removed from around extension 52 of handle 26, and housing 30 can be removed. Alternatively, if clip 112 and operating portion 22 with end 32 are of metal or other autoclaveable materials, they could remain connected to handle 26, although it will be seen that separation of these parts will likely enable more thorough cleaning and sterilization of these parts. Following autoclaving of handle 26 and/or housing 30, tool 20 can be reassembled substantially as indicated above. A new cable 24 may be connected to insert 62, or as indicated above, in proper conditions part of the prior cable 24 can be reused. If a portion has been cut from a prior cable 24, or if a new cable 24 is provided, an end 45 may be stripped using insert 62, as discussed above.

Operating end 22 and its electrodes 34 or operating end 32 may be made of a variety of sturdy biocompatible surgical-grade materials, including metals such as titanium and stainless steel. Other non- or minimally-corrosive conductive materials can be used for end 32.

While the disclosure has been illustrated and described in detail in the drawings and foregoing description, the same is to be considered as illustrative and not restrictive in character, it being understood that all changes and modifications that come within the spirit of the disclosure are desired to be protected. Directional terms used herein, such as "above," "below" or similar terms, are not intended to be necessarily indicative of the orientation of the described feature in all situations. Rather, they are used in conjunction with the figures to indicate general relationships between or among features.

What is claimed is:

1. A handle for a surgical tool, comprising:
    a body portion having an exterior surface and first, second and third holes each having separate openings through the exterior surface, said second hole being sized to accommodate an electrical conductor, and said third hole being at least partially threaded;
    an insert member removably placed in said first hole, said insert member having a cap portion that is substantially flush with the exterior surface of said body portion when said insert member is placed in said first hole, said insert member further having a pair of arms distal of said cap for stripping covering from an electrical conductor; and
    a set screw threaded into said third hole, wherein said first hole and said third hole communicate with said second hole, and neither of said first hole and said third hole are parallel or concentric with said second hole; and
    an extension portion extending from said body portion and adapted to connect to a tool shaft, said extension portion having an aperture that communicates with said second hole.

2. The apparatus of claim 1, further comprising a substantially C-shaped clip around at least part of said extension.

3. The apparatus of claim 1, wherein at least a portion of said exterior surface of said body portion is substantially spherical, and said extension portion extends substantially radially from said spherical surface.

4. The apparatus of claim 1, wherein a washer is fitted into said second hole, said washer having an opening for a cable.

5. The apparatus of claim 1, wherein said at least a portion of said exterior surface is substantially spherical, and said second hole is oriented substantially radially with respect to said surface, and said first hole and said third hole are oriented non-radially with respect to said surface and substantially perpendicular to said second hole.

6. The apparatus of claim 5, wherein said first hole and said third hole meet at substantially the same point along said second hole.

7. The apparatus of claim 1, wherein said cap has a perimeter that is part convex and part concave.

8. The apparatus of claim 1, wherein said insert member includes a medial portion between said cap and said arms, and said medial portion includes at least one hole.

9. The apparatus of claim 1, wherein at least said body portion of said handle is made of a substance that is autoclaveable without substantial change in its physical characteristics.

10. The apparatus of claim 9, wherein said substance is polyoxymethylene.

11. The apparatus of claim 9, wherein said handle is made of a compressible substance.

12. A tool for use in spinal orthopedic surgery, comprising:
    a handle according to claim 1;
    a housing connected to said handle, said housing having an operating end with at least one electrode and at least one conductor electrically connected to said at least one electrode and electrically connected to said insert member of said handle; and
    a cable connected to said handle, said cable extending through said second hole of said handle, said cable having a first end with a plug, a second end, and at least one electrical conductor, said conductor of said cable being electrically connected to said insert member of said handle.

13. The apparatus of claim 12, further comprising an electrical power source, said plug being connected to said power source.

14. The apparatus of claim 12, further comprising a detector for detecting and analyzing electrical signals, said plug being connected to said detector.

15. The apparatus of claim 12, wherein said housing is insertable into said aperture in said extension portion.

16. The apparatus of claim 15, wherein said at least a portion of said exterior surface of said handle is substantially spherical, said extension portion extending substantially radially from said exterior surface, and further comprising a clip having an internal diameter smaller than at least a portion of said extension portion, wherein said clip retains said housing within said handle.

17. A handle for a surgical tool that uses electricity, comprising:
   a body portion having at least a part that is substantially spherical;
   an extension portion having at least a part that is substantially cylindrical, said extension portion adapted to connect to a tool shaft;
   an insert member removably inserted into said body portion, said insert member having a cap portion having a perimeter that has a convex portion and a concave portion, said insert member further having a distal portion including two arms configured for stripping wire or cable;
   said body portion including a first hole adapted to accommodate a wire or cable, wherein said body enables electricity to be passed from a wire or cable in said first hole to a shaft extending from said extension; and
   said body portion having a second hole communicating with said first hole, said second hole being at least partially threaded and a set screw threaded into said second hole to a position in or adjacent to said first hole.

18. The apparatus of claim 17, wherein at least a portion of said insert member is made of an electrically-conductive material.

19. The apparatus of claim 17, wherein said set screw is threaded into said second hole to a position wherein a portion of said set screw is positioned in said first hole.

20. The apparatus of claim 17, further comprising a washer inserted into said first hole.

21. The apparatus of claim 17, wherein said extension portion includes a channel, and further comprising a clip member inserted into said channel.

22. The apparatus of claim 21, wherein said channel has a bottom surface that defines a minor diameter of said extension, said clip member is substantially C-shaped and defines an inner diameter, and said inner diameter is smaller than said minor diameter.

23. The apparatus of claim 17, wherein said handle is autoclaveable without substantial change in its physical characteristics.

24. The apparatus of claim 23, wherein said handle is made of polyoxymethylene.

25. The apparatus of claim 23, wherein said handle is made of a compressible substance.

26. A handle for a surgical tool, comprising:
   a body portion having an exterior surface and first, second and third holes each having separate openings through the exterior surface, said second hole being sized to accommodate an electrical conductor, and said third hole being at least partially threaded;
   an insert member removably placed in said first hole, said insert member having a cap portion that is substantially flush with the exterior surface of said body portion when said insert member is placed in said first hole, said insert member further having a pair of arms distal of said cap for stripping covering from an electrical conductor; and
   a set screw threaded into said third hole, wherein said first hole and said third hole communicate with said second hole, and neither of said first hole and said third hole are parallel or concentric with said second hole; and
   an extension portion extending from said body portion and having at least a part that is substantially cylindrical, said extension portion adapted to connect to a tool shaft.

27. The apparatus of claim 26, wherein said extension portion has an aperture adapted to receive the tool shaft.

28. The apparatus of claim 27, wherein said aperture communicates with said second hole.

29. The apparatus of claim 26, wherein said extension portion includes a channel, and further comprising a clip member inserted into said channel.

30. The apparatus of claim 29, wherein said clip member is-substantially C-shaped.

31. The apparatus of claim 26, wherein at least a portion of said exterior surface of said body portion is substantially spherical, and said extension portion extends substantially radially from said spherical surface.

* * * * *